US010918731B2

(12) United States Patent
Liu et al.

(10) Patent No.: US 10,918,731 B2
(45) Date of Patent: Feb. 16, 2021

(54) HSP90 INHIBITORY PEPTIDE CONJUGATE AND APPLICATION THEREOF IN TREATING TUMOR

(71) Applicant: INSTITUTE OF BASIC MEDICAL SCIENCES, CHINESE ACADEMY OF MEDICAL SCIENCES, Beijing (CN)

(72) Inventors: Yanyong Liu, Beijing (CN); Nan Yang, Beijing (CN); Pingping Zuo, Beijing (CN)

(73) Assignee: INSTITUTE OF BASIC MEDICAL SCIENCES, CHINESE ACADEMY OF MEDICAL SCIENCES, Beijing (CN)

(*) Notice: Subject to any disclaimer, the term of this patent is extended or adjusted under 35 U.S.C. 154(b) by 299 days.

(21) Appl. No.: 15/563,042

(22) PCT Filed: Oct. 14, 2015

(86) PCT No.: PCT/CN2015/091888
§ 371 (c)(1),
(2) Date: Sep. 29, 2017

(87) PCT Pub. No.: WO2016/173214
PCT Pub. Date: Nov. 3, 2016

(65) Prior Publication Data
US 2019/0365911 A1 Dec. 5, 2019

(30) Foreign Application Priority Data
Apr. 27, 2015 (CN) .......................... 2015 1 0203194

(51) Int. Cl.
*A61K 47/64* (2017.01)
*A61P 35/00* (2006.01)
*A61K 31/337* (2006.01)
*A61K 31/704* (2006.01)
*A61K 38/08* (2019.01)

(52) U.S. Cl.
CPC ............ *A61K 47/64* (2017.08); *A61K 31/337* (2013.01); *A61K 31/704* (2013.01); *A61K 38/08* (2013.01); *A61P 35/00* (2018.01)

(58) Field of Classification Search
CPC .... A61K 31/337; A61K 31/704; A61K 38/08; A61K 47/64; A61P 35/00; A61P 43/00
See application file for complete search history.

(56) References Cited

U.S. PATENT DOCUMENTS

| 6,399,575 B1 | 6/2002 | Smith et al. | |
| 8,268,962 B2 * | 9/2012 | Heemskerk | A61P 3/10 |
| | | | 530/329 |
| 8,703,729 B2 * | 4/2014 | Schlingensiepen | A61P 43/00 |
| | | | 514/44 A |
| 2005/0187147 A1 | 8/2005 | Newman et al. | |
| 2009/0246211 A1 * | 10/2009 | Henri | A61K 47/64 |
| | | | 424/181.1 |

FOREIGN PATENT DOCUMENTS

| CN | 101792487 | 8/2010 |
| CN | 102127154 | 7/2011 |
| CN | 102219812 | 10/2011 |
| CN | 103040850 | 4/2013 |
| CN | 103342735 | 10/2013 |
| CN | 104800858 | 7/2015 |
| JP | 2006510360 | 3/2006 |
| JP | 2007509978 | 4/2007 |
| JP | 2009508852 | 3/2009 |
| JP | 2013527157 | 6/2013 |
| WO | WO 2013/158644 | 10/2013 |
| WO | WO 2014/080251 | 5/2014 |

OTHER PUBLICATIONS

Hensbergen et al. A doxorubicin-CNGRC peptide conjugate with prodrug properties. Biochemical Pharmacology. vol. 63, pp. 897-908. (Year: 2002).*
Orosz et al. Novel nontoxic heat shock protein 90 inhibitors having selective antiproliferative effect . The International Journal of Biochemistry & Cell Biology. vol. 38, pp. 1352-1362. (Year: 2006).*
Bertin et al. High-density doxorubicin-conjugated polymeric nanoparticles via ring-opening metathesis polymerization. Chem Comm. pp. 3793-3795. (Year: 2005).*
Pike et al. HPMA copolymer-cyclic RGD conjugates for tumor targeting. Adv Drug Delivery Rev. vol. 62, pp. 167-183. (Year: 2010).*
Porter et al. Discovery and development of Hsp90 inhibitors: a promising pathway for cancer therapy. Current Opinion in Chemical Biology. vol. 14, pp. 412-420. (Year: 2010).*
International search report dated Feb. 16, 2016, and Written Opinion dated Jan. 27, 2016 and English translation from corresponding application No. PCT/CN2015/091888.
Office Action dated Mar. 3, 2017 from corresponding application No. CN 201510203194.X.
Office Action dated May 10, 2017 from corresponding application No. CN 201510203194.X.
Ferrarini et al., "Unusual Expression and Localization of Heat-Shock Proteins in Human Tumor Cells", Int. J. Cancer: 51, 613-619 (1992), Wiley-Liss, Inc.; total 8 pages.
Becker B et al., "Induction of Hsp90 protein expression in malignant melanomas and melanoma metastases", Experimental Dermatology 2004: 13: 27-32, Blackwell Munksgaard; total 6 pages.

(Continued)

*Primary Examiner* — Marcela M Cordero Garcia
(74) *Attorney, Agent, or Firm* — Hauptman Ham, LLP

(57) ABSTRACT

The invention discloses a conjugate constructed by conjugating a HSP90 inhibitory peptide to cytotoxic agent via linker and use thereof in the preparing medicine for preventing and/or treating tumor. The mentioned conjugates possess triple anti-tumor effects including targeting delivery, chemotherapy and apoptosis-promotion, which can enhance the anti-tumor efficacy, reduce the dosage, and decrease the toxicity induced by accumulation of chemotherapeutics.

16 Claims, 8 Drawing Sheets

Figure 1:
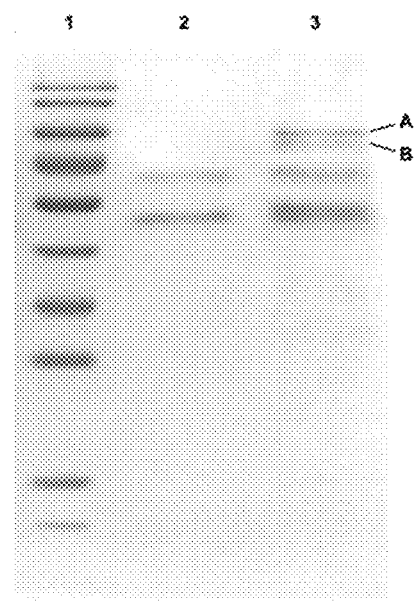

Specification includes a Sequence Listing.

(56) References Cited

OTHER PUBLICATIONS

Zhao et al., "Navigating the Chaperone Network: Resource An Integrative Map of Physical and Genetic Interactions Mediated by the Hsp90 Chaperone", Cell, vol. 120, 715-727, Mar. 11, 2005, Elsevier Inc.; total 13 pages.

First Office Action dated Mar. 3, 2017 and English translation from corresponding application No. CN 201510203194.X.

First Search dated Feb. 3, 2017 and English translation from corresponding application No. CN 201510203194.X.

Second Office Action dated May 10, 2017 and English translation from corresponding application No. CN 20151023194.X.

Notification of Reasons for Refusal dated Mar. 27, 2018 with English translation from corresponding application No. 2017-549252.

Search Report dated Apr. 5, 2018 from corresponding application No. EP 15890589.3.

Fischer, Christiane et al., "Bombesin-Shepherdin Radioconjugate Designed for Combined Extra and Intracellular Targeting", Pharmaceuticals, vol. 7, No. 6, May 27, 2014, pp. 662-675.

Notification of reasons for refusal dated Aug. 20, 2018 and English translation from corresponding application No. JP 2017-549252.

Joseph Molnar et al., "Effects of Nontoxic Heat Shock Protein 90 Inhibitor Peptide Derivatives on Reversal of MDR of Tumor Cells", in Vivo 2L: 429-433 (2007).

Office Action dated Dec. 8, 2017 and English translation from corresponding application No. KR 10-2017-7025806.

Notification to Grant Patent Right for Invention dated Sep. 26, 2017 and English translation from corresponding application No. CN 201510203194.X.

\* cited by examiner

HSP90 INHIBITORY PEPTIDE CONJUGATE AND APPLICATION THEREOF IN TREATING TUMOR

RELATED APPLICATIONS

The present application is a National Phase of International Application Number PCT/CN2015/091888, filed Oct. 14, 2015, and claims the priority of China Application No. 201510203194.X, filed Apr. 27, 2015.

TECHNICAL FIELD

The present invention relates to targeting agents for tumor treatment, particularly, relating to the use of Heat Shock Protein 90 (HSP90) inhibitory peptide in preparing targeting therapeutic conjugates for treating tumors.

INCORPORATION BY REFERENCE

The sequence listing provided in the file entitled INC1SEQUENCELISTING-PCT-CN2015-091888_M.txt, which is an ASCII text file that was created on Jun. 13, 2019, and which comprises 583 bytes, is hereby incorporated by reference in its entirety.

BACKGROUND ART

Malignant tumor seriously threatens the human health and improving the present therapeutic efficacy is an important mission for the medical researchers. Most of the current available chemotherapeutics exhibits a poor targeting capability with only 5-10% of administrated dosage accumulated in the tumor sites. Meanwhile, severe adverse side effects of these drugs also affect the optimized dosage, leading to incomplete recovery, relapse and drug resistance.

Tremendous clinical advances achieved for the tyrosine kinase inhibitors aiming at the specific mutation of signaling pathway in tumor tissues. For the people carrying genetic mutated phenotype, the molecularly targeted drugs are obviously effective with low adverse effects. However, molecularly targeted cancer therapy remains challenged by an extremely small proportion of patients that can benefit and the occurrence of drug resistance 10-12 months later. Cancer cells often find ways to compensate or replace for the blockage of the pathway, therefore pinpointing a single pathway is unlikely to eradicate cancer cells. Researchers pay more attention to the signal converging point and trying to developing drugs that simultaneously attack multiple targets to improve the therapeutic efficacy and action spectrum. In this regard, heat shock protein 90 (Hsp90) represents an attractive cancer therapeutic target.

Hsp90 is an abundant and ubiquitous molecular chaperone in the eukaryotic cell that plays an important role in regulating correct folding, maturation and stabilization of numerous nascent client proteins including enzyme, receptor and signal molecular. The cancer cells initiate protective mechanisms to antagonize the challenge of chemotherapeutics, including the rapid up-regulation of HSP90, which constitute the basis for chemotherapy adaption and resistance. Accordingly, Hsp90 is constitutively expressed at 2-10 fold levels in cancer cells than their normal counterparts W. Moreover, HSP90 is also highly expressed on the cancer cell surface [2]. About tens of oncogenic components are the client protein of HSP90, which make it important oncogenic signal converging point [3]. Inhibiting Hsp90 function will lead to degradation of multiple oncogenic proteins. HSP90 also participates the response to chemotherapeutics by regulating the autophagy, therefore inhibiting HSP90 is facilitated to improve the antitumor efficacy.

As stated in authorized patent (Patent Number: ZL201310258476.0; Patent Title: A tumor specific targeting peptide and thereof use), a targeting peptide (Amino acid sequence: LPLTPLP (SEQ ID No: 1), hereinafter referred to as P7) was screened by phage display technique, and was conjugated to the Docetaxel-loaded polylactic acid nanoparticles for the preparation of medicines for early diagnosis and treatment. The conjugated nanoparticle obtained from the targeting peptide and the Docetaxel-loaded polylactic acid was hereinafter referred to as targeting nanoparticle preparation (TN-DTX).

DESCRIPTION OF THE INVENTION

Cellular membrane proteins were extracted by the applicants and the binding proteins were separated using polyacrylamide gel electrophoresis. Then, the isolated binding protein of targeting peptide was identified as HSP90 with amino acid sequence of LPLTPLP (SEQ ID No: 1) (hereinafter referred to as targeting peptide) by mass spectrometry analysis. The impact of the targeting peptide on the expression of HSP90 was carried out by Western Blotting analysis, results showed that targeting peptide directly inhibited the expression of HSP90 after the exposure of tumor cell to the targeting peptide, indicating that the targeting peptide was a HSP90 inhibitory peptide.

As stated in the background art section, HSP90 was highly expressed in a variety of tumor cell to defense the external stress such as temperature, drug and radiation, playing a vital role in the recurrence and drug resistance. Applicants explored the combinative effect of targeting peptide with Docetaxel, which was referred to as DTX hereinafter.

Combining docetaxel with targeting peptide significantly affected the expression of the autophagy-associated protein Beclin 1 and LC3. Exposure to targeting peptide alone did not affect the expression of those two proteins. Following exposure to docetaxel, the expression of the autophagy-associated protein Beclin 1 increased and the conversion of LC3-I to LC3-II occurred, indicating an elevation of autophagy. Simultaneous administrating docetaxel with LPLTPLP (SEQ ID No: 1) led to a decrease in the expression of beclin 1 and the reversal of the LC3-I to LC3-II conversion compared with docetaxel alone. The obtained results showed that the targeting peptide significantly inhibited the autophagy induced by docetaxel.

As can be seen that in addition to targeting capability, targeting peptide also can enhance the switching of tumor cell from autophagy to apoptosis when combined with docetaxel, leading to enhanced antitumor effect. Based on this background, a conjugate capable of targeting delivery, autophagy inhibition and cancer killing was constructed by conjugating the targeting peptide with docetaxel (hereinafter referred to as DTX-P7).

As stated in vivo experiment in the invention, DTX-P7 significantly decreased the tumor volume compared with docetaxel and nanoparticle prepared based on the targeting peptide, exhibiting obvious cytotoxic effects to lung adenocarcinoma, breast cancer and melanoma cells.

The invention provides the use of employing the HSP90 inhibitory peptide for the preparing the cytotoxic agent conjugates. The HSP90 inhibitory peptide specifically binds to cancer cells and suppresses the intracellular expression of HSP90.

This invention further provides a conjugate which is constructed by conjugating HSP90 inhibitory peptide with cytotoxic agent through a linker. Preferably, the amino acid sequence of the HSP90 inhibitory peptide is LPLTPLP (SEQ ID No: 1). Preferably, there are 1-3 G linked at the amino terminal of the HSP90 inhibitory peptide, and S, SH or SHS linked at the carboxyl terminal of the HSP90 inhibitory peptide. Preferably, the cytotoxic agents are selected from docetaxel, paclitaxel and doxorubicin. Preferably, the general formula of described linker is —CO—,$CH_2CH_2$,n— CO— where n is selected from 1, 2, 3, 4, 5, 6, 7, 8, 9, or 10. The preferable formula of the linker is —CO—$CH_2CH_2$—CO—.

This invention provides the preparation of conjugates employing HSP90 inhibitory peptide and cytotoxic agents such as docetaxel, paclitaxel and doxorubicin, through esterification or amidation reaction mediated by the linker. Preferably, the amino terminal of the peptide is connected to the 2-OH of docetaxel and paclitaxel mediated by the linker to prepare the conjugate.

In other respect, this invention provides a conjugate by linking amino terminal of HSP90 inhibitory peptide to the 3-$NH_2$ on the 10-lyxo-hexopyranosyl group of the doxorubicin mediated by the linker.

In another aspect, this invention provides a conjugate by linking amino terminal of HSP90 inhibitory peptide to the 8-glycolyl group of the doxorubicin mediated by the linker.

The present invention relates to the drugs using the conjugates mentioned above as active ingredient. The conjugates are combined with pharmaceutically acceptable solid or liquid excipients and/or supplements to prepare any formulations applicable to human or animal. Furthermore, this invention relates to the use of conjugates for preparing the cancer preventive and/or therapeutic drugs. The tumors refer to HSP90 highly-expressed cancer, preferably, comprising lung cancer, lung adenocarcinoma, melanoma, gastric cancer, breast cancer, renal carcinoma, liver cancer, oral epidermoid carcinoma, cervical cancer, ovarian cancer, pancreatic cancer, prostate cancer, colorectal cancer and neural tumors, more preferably, lung adenocarcinoma, breast cancer and melanoma, most preferably, lung adenocarcinoma.

The conjugates in this invention can be administrated in way of unit dose. The administrated routes include intestinal and parenteral routes, such as oral administration, intravenous injection, intramuscular injection, subcutaneous injection and trans-nasal, oral mucosa, eye, pulmonary, dermal, vaginal and rectal administration, and so on.

The compositions can be administrated in a liquid, solid or semi-solid formulation. Liquid formulation comprises the solution (including true solution and colloidal solution), emulsion (o/w, w/o, or multiple emulsion), suspension, injection (including injection workshop, powder injection and infusion solution), eye-drops, nasal-drops, lotion, liniment and so on. Solid formulation includes tablet (including conventional, enteric-coated, buccal, dispersible, chewable, effervescent, orally disintegrating tablets), capsule (including hard, soft or enteric capsule), granules, powder, pellet, dropping pill, suppository, membranes, paster, aerosol or dry powder inhalations, spray and so on. Semisolid formulation comprises ointment, gel, cataplasm and so on.

The conjugate can be made into either commonly used preparations, or sustained release, controlled release, targeting preparation and diverse microparticle drug delivery system.

To prepare the tablet formulation, the widely-known excipients including diluent, adhesive, wetting agent, disintegrant, lubricant, glidant can be used together with the conjugate. The diluent includes starch, dextrin, sucrose, glucose, lactose, mannitol, sorbitol, newtol, microcrystalline cellulose, calcium sulfate, calcium hydrophosphate, calcium carbonate, and so on. Wetting agent comprises water, ethanol, isopropanol, and so on. The adhesive includes starch slurry, dextrin, syrup, honey, glucose solution, microcrystalline cellulose, arabic gum, gelatin, sodium carboxymethylcellulose, methylcellulose, hydroxypropyl methyl cellulose, ethyecellulose, acrylic resin, Carbopol, polyvinylpyrrolidone, polyethylene glycol, and so on. The disintegrant includes the dry starch, microcrystalline cellulose, low substituted hydroxypropyl cellulose, cross-linked polyvinylpyrrolidone, polyoxyethylene sorbitol aliphatic ester, sodium dodecyl sulfate and so on. Lubricant and glidant comprises talcum powder, silica, stearate, tartaric acid, liquid paraffin, polyethylene glycol and so on.

The tablet formulation can be further prepared to the coating tablet, such as sugar-coating, film-coated, enteric-coated, double-layer or multilayer tablet.

To prepare the composition into capsule formation, the conjugate can be mixed with diluent, glidant and directly packaged into hard or soft capsules. The conjugate can also be mixed with the diluent, adhesive, disintegrant to prepare the granule or pellet, and packaged into hard or soft capsules. The diluent, adhesive, wetting agent, disintegrant, glidant used to prepare the tablet can also be applicable to the capsule formulation.

This conjugate can be used to prepare the injection formulation with water, ethanol, isopropanol, propanediol or the mixture thereof as solvent and adding routinely used solubilizer, cosolvent, pH regulator osmotic pressure regulator. The solubilizer or cosolvent includes poloxamer, phosphatidylcholine, hydroxypropyl-β-cyclodextrin and so on. The pH regulator comprises phosphate, acetate, hydrochloric acid, sodium hydroxide and so on. The osmotic pressure regulator is comprised of sodium chloride, mannitol, glucose, phosphate, acetate, and so on. To prepare the freeze-dried powder injection, mannitol and glucose can be used as propping agent.

Moreover, colorant, preservative, perfume, flavor and other additives can be supplemented if needed.

The composition may be administrated via any of widely known route, as long as it is able to reach a desired effect.

The conjugates in the invention may be used individually or combined with other therapeutics or expectant drugs.

The anti-tumor effect of the conjugates has been confirmed to treat the malignant cancer.

This invention discloses that conjugates prepared by coupling HSP90 with cytotoxic agents such as docetaxel, paclitaxel and doxorubicin, are promising and valuable to enhance the anti-tumor efficacy, meanwhile reduce the dosage, which can lessen the adverse effect caused by chemotherapeutics accumulation. The conjugates exhibit triple anti-tumor effects: targeting delivery, chemotherapy, and promoting apoptosis, holding a great potential to improve the clinical outcome of a variety of tumors and reverse the drug resistance.

LEGEND ILLUSTRATION

FIG. 1 shows that the binding protein of targeting peptide is HSP90.

Figure 2A:
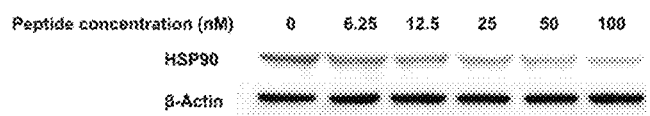
Figure 2B:
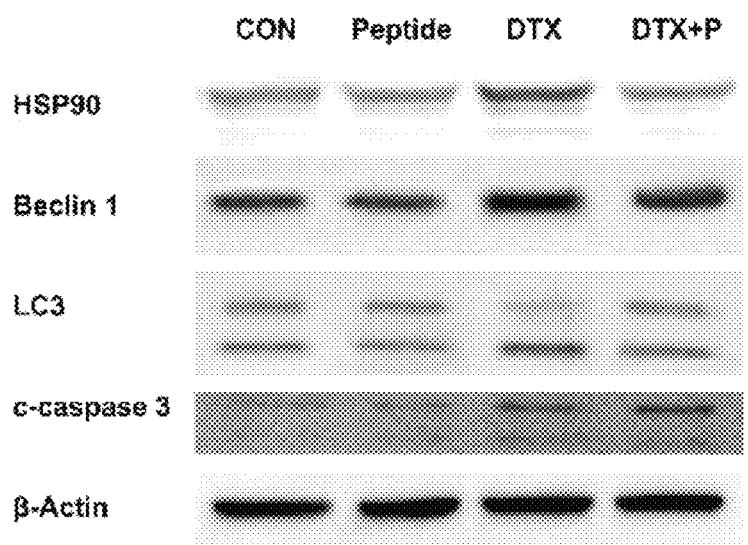
Figure 2:
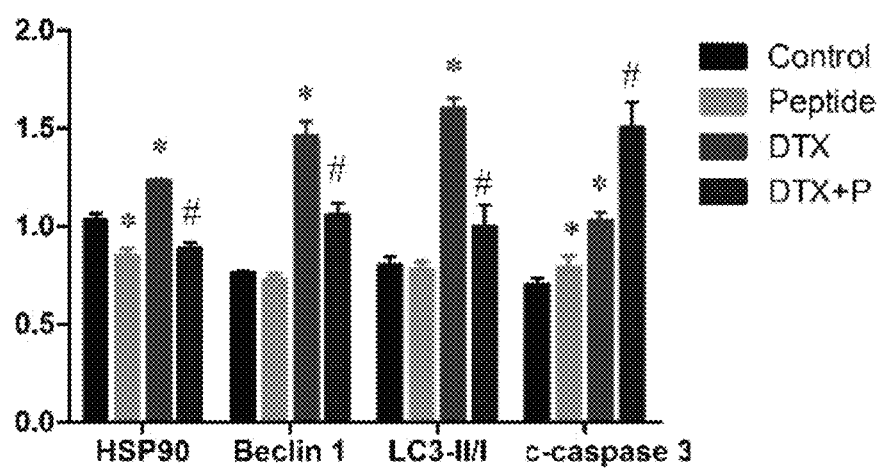
Figure 2:
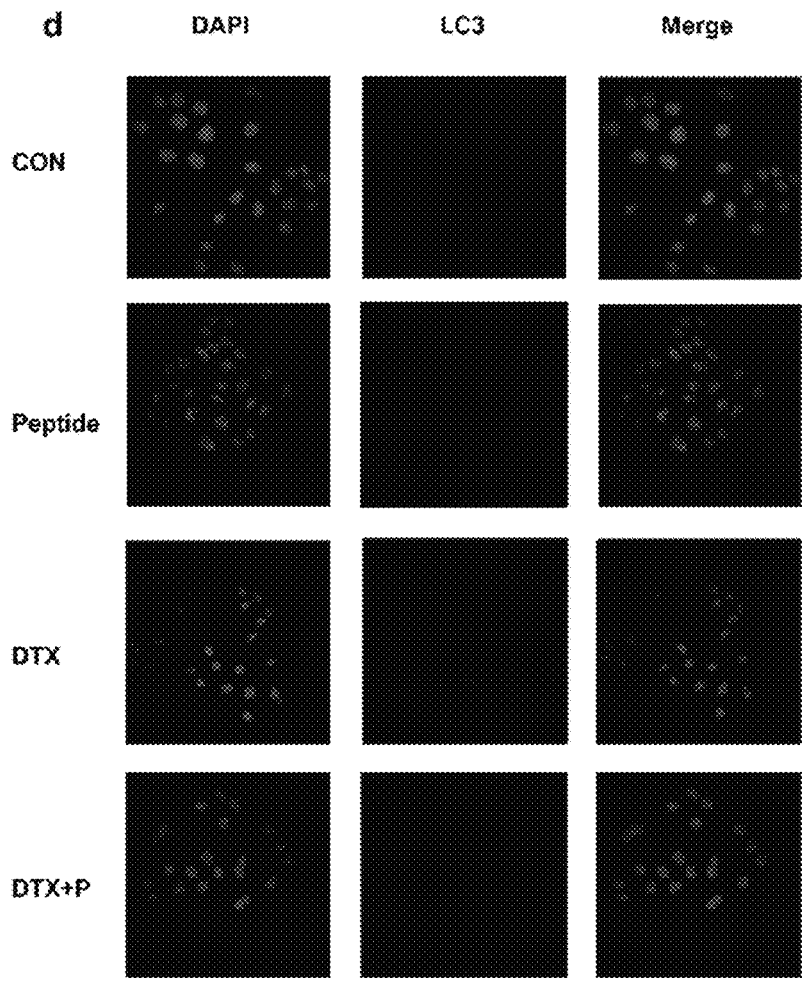
Figure 2E:
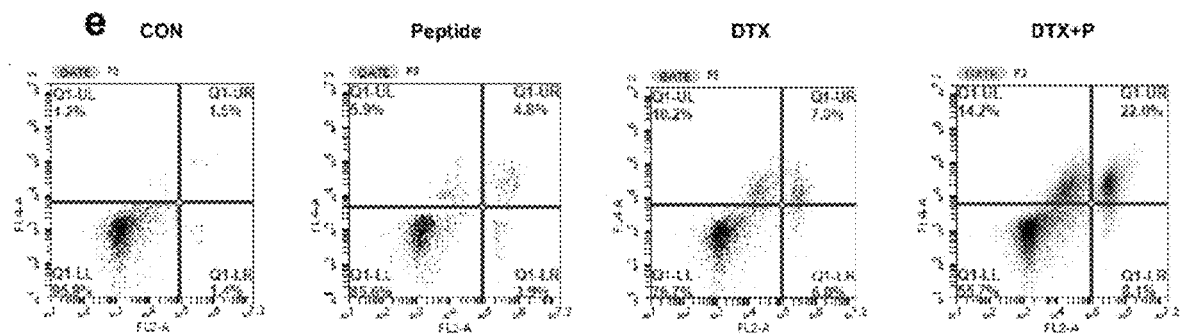
Figure 2:
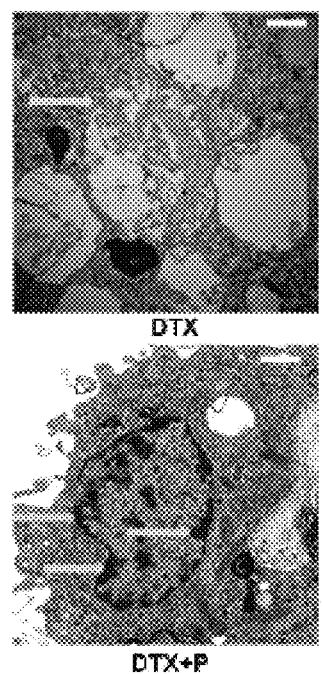

FIG. 2A-2F present the effects of targeting peptide on the HSP90 expression, autophagy and apoptosis. FIG. 2A shows the Western blotting results, indicating that targeting peptide significantly inhibited the expression of HSP90 in a dose-dependent manner Results in FIG. 2B-2D indicated that targeting peptide obviously inhibited the autophagy induced by docetaxel. FIG. 2E showed that targeting peptide promoted the apoptosis induced by docetaxel by Annexin V analysis. FIG. 2F showed that the apoptosis-enhancing effect was further confirmed by transmission electron microscope observation.

Figure 3:
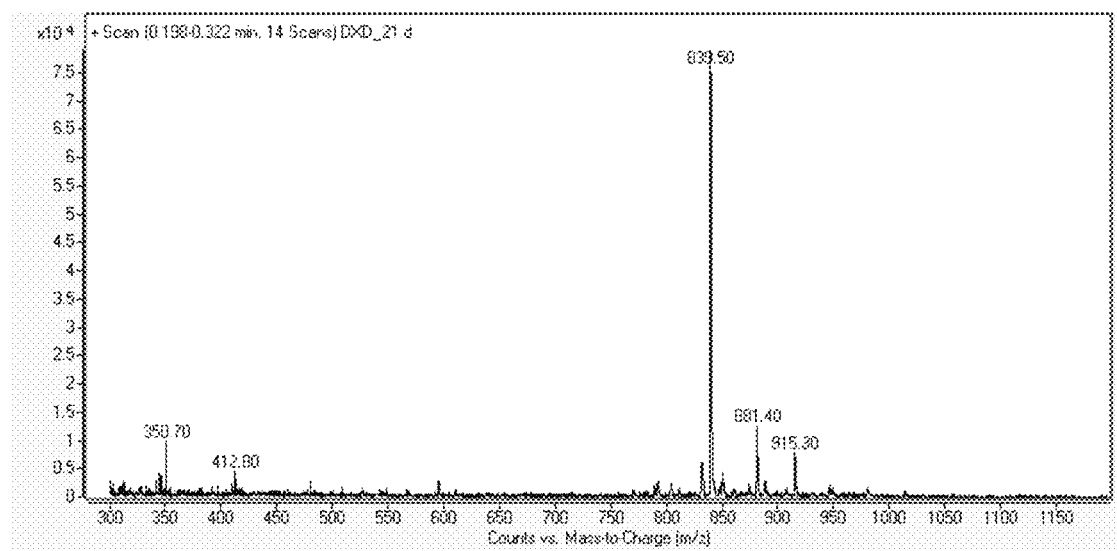

FIG. 3 refers to the mass spectrometry of DTX-P7.

Figure 4:
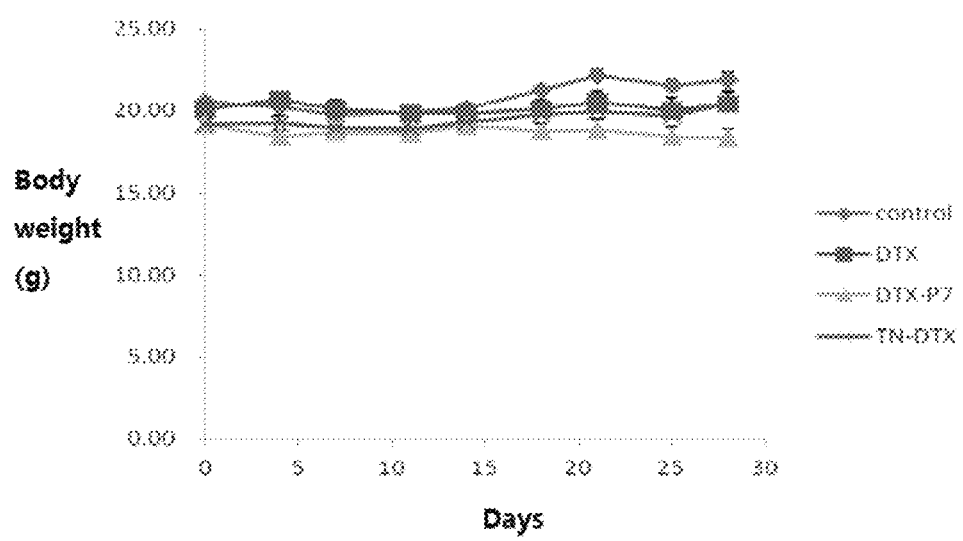

FIG. 4 refers to the body weight changes of nude mice in the different groups.

Figure 5:
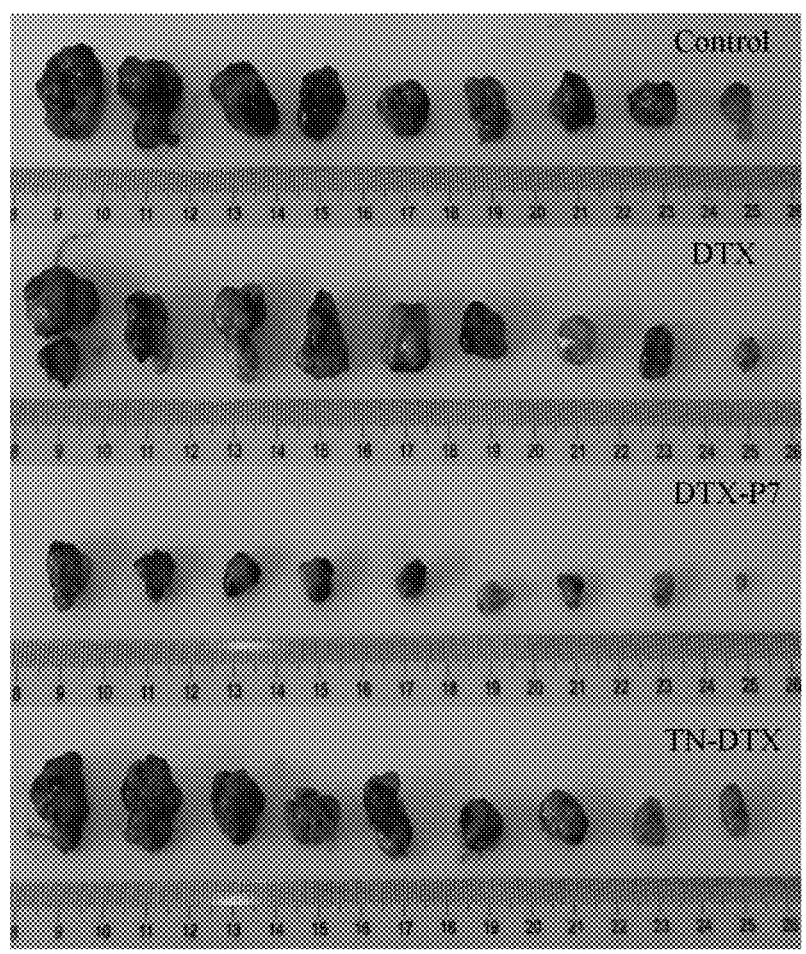

FIG. 5 refers to the tumor tissues resected from DTX, DTX-P7, TN-DTX treated groups.

Figure 6:
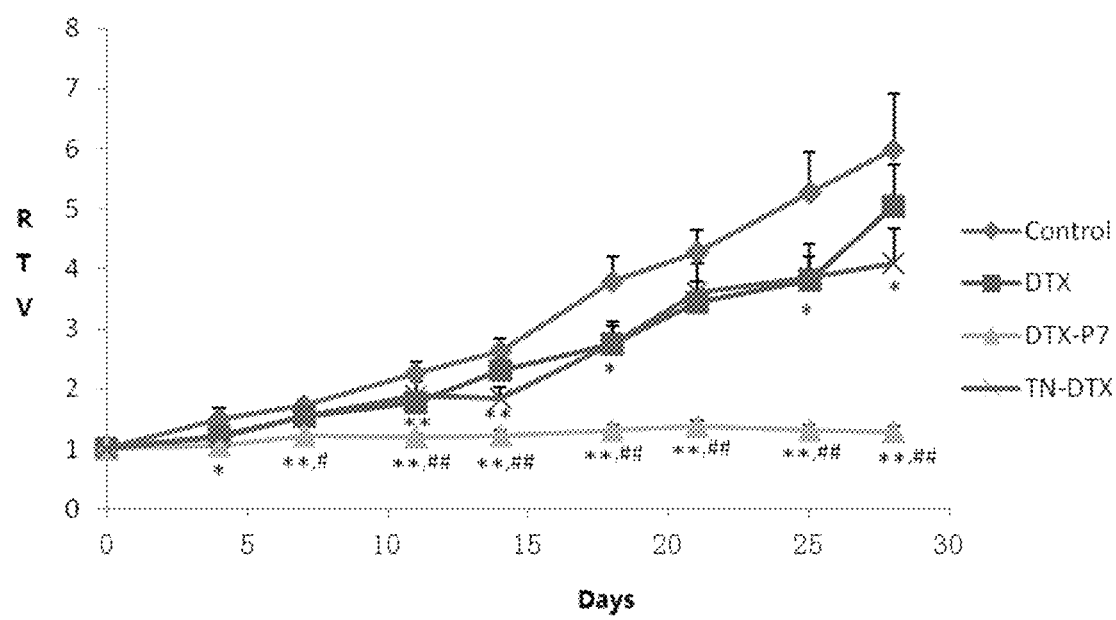

FIG. 6 refers to the relative volume of the tumors from DTX, DTX-P7, TN-DTX treated groups.

Herein, *: referring to comparison with control group; # referring to comparison with DTX and TN-DTX groups.

EMBODIMENTS

The following embodiments furthermore illustrate the content of this invention, but understandably should not be interpreted as in any way limiting its scope. It will be understood by those skilled in the art that the present invention may be implemented in a different specific form without changing the technical spirit or essential characteristics thereof. Therefore it should be understood that all changes and modifications to the methods, procedures or conditions that are derived from the subject matter defined in the claims or equivalents thereof are intended to be embraced in the scope of the present invention. Unless specialized, the employed techniques in the present invention are conventional methods for those skilled in the art.

Embodiment 1: Binding Protein of Targeting Peptide and its Effect on the HSP90 Expression The protein was extracted with protein extraction kit and subjected to SDS-Page electrophoresis. The interesting protein was recovered and digested with trypsin, then analyzed by mass spectrometry. As shown in FIG. 1, molecular weight of band A was 53 Kd, which was consistent with that of HSP90 kDa. Molecular weight of band B was 48 Kd, consistent with that of HSP90 kDβ. Therefore, the target of peptide is identified as HSP90 (FIG. 1).

Embodiment 2: Effect of Targeting Peptide on the Expression of HSP90

(1) lung adenocarcinoma A549 cells were trypsinized and then centrifuged at 800×g for 5 min. The precipitate was re-suspended with PBS and adjusted to $1 \times 10^6$ cells/ml.

(2) the cells were seeded into 6-well plate and 2 ml culture medium was added. Then the cells were incubated at 37° C., 5% $CO_2$ overnight.

(3) The peptide was diluted with medium and 300 μl solution was added to each well with a final concentration of $1 \times 10^{-4}$ M. Equal volume of medium was added to the negative well. Triple wells were set for each group and experiment was repeated three times. The plate was incubated at 37° C., 5% $CO_2$ for 48 h. Protein was extracted and subjected to Western blotting analysis.

Results showed that targeting peptide effectively down regulated the expression of HSP90 in a dose-dependent manner (FIG. 2A), indicating the peptide is a HSP90 inhibitory peptide.

Embodiment 3: Effect of Targeting Peptide on the Apoptosis

The cells were seeded and cultured. Targeting peptide was diluted with culture medium. Appropriate concentration of DTX was also prepared for the seeded cells. Equivalent culture medium was added as negative control group, $1 \times 10^{-9}$ M targeting peptide solution added as Peptide group, $10^{-9}$ M DTX added as DTX group, $10^{-9}$ M targeting peptide and $10^{-4}$ M DTX added as combination group (DTX+P). The cells were incubated at 37° C., 5% $CO_2$ for 6 h to analyze the apoptosis by Annexin V method. The protein was extracted to measure the expression of apoptosis related proteins.

Results of annexin V showed that targeting peptide induced apoptosis and further promoted apoptosis when combined with DTX.

Western blotting analysis showed that targeting peptide induce caspase-3 cleavage and the cleavage was further enhanced when combined with DTX compared with DTX alone. Targeting peptide promoted apoptosis and enhanced the apoptosis induced by DTX (FIG. 2E, F)

Embodiment 4: Effect of Targeting Peptide on the Autophagy

The cells were seeded and cultured. Targeting peptide was diluted with culture medium. Appropriate concentration of DTX was also prepared for the seeded cells. Equivalent culture medium was added as negative control group; $1 \times 10^{-9}$ M targeting peptide solution was added as Peptide group; $10^{-9}$ M DTX was added as DTX group; $10^{-9}$ M targeting peptide and $10^{-4}$ M DTX were added as combination group (DTX+P). The cells were incubated at 37° C., 5% $CO_2$ for 6 h to analyze the autophagosome. Protein was extracted to measured expression of autophagy related proteins.

FIG. 2B-FIG. 2D showed that the expressions of autophagic Beclin1 and LC3 were changed by DTX and targeting peptide treatment. Targeting peptide treatment alone did not affect the expression of these proteins. DTX enhanced the expression the Beclin 1 and conversion of LC3-I to LC3-II, indicating an elevated increase in autophagy. Compared with the DTX treatment only, Beclin1 expression and conversion of LC3-I to LC3-II decreased when DTX and targeting peptide were simultaneously added, suggesting that targeting peptide significantly inhibited the autophagy induced by DTX.

Embodiment 5: Preparation of DTX and HSP 90 Inhibitory Peptide Conjugates (DTX-P7)

Synthesis of DTX-Suc

DTX (1.5 g) and succinic anhydride (abbreviated as Suc, 0.5 g) were dissolved in $CH_2Cl_2$ (20 mL). After pyridine (0.5 ml) was added, the mixture was stirred for 1 week at room temperature. The reaction mixture was concentrated in a vacuum to remove the $CH_2Cl_2$, 50 ml 5% citric acid solution was added and then extracted with 50 ml ethyl acetate for 3 times. Then obtained organic phase was distillated to remove ethyl acetate. The crude DTX-Suc was further subjected to C18 preparative chromatography for purification and freeze. Preparative chromatography method: mobile phase: 40-70% acetonitrile (60-30% water)/0-30 min, flow rate of 20 ml/min Analytical chromatography Synthesis of DTX-P7

DTX-P7 conjugates were prepared using the solid-phase peptide synthesis method. The amino acid was successively linked onto the 0.83 g Fmoc-Pro-Trt resin (substitution degree of the resin was 0.6 mmol/g). After the peptide bond constructed, DTX-Suc was linked to the N terminal of the peptide chain. The crude conjugates dissociated from the resin was purified with preparative C18 column. The targeted fraction was collected and lyophilized to obtain the DTX-P7, and subsequently submitted to further HPLC and mass spectrometry analysis. Preparative chromatography method: mobile phase: 40-70% acetonitrile (60-30% water)/ 0-30 min, flow rate of 20 ml/min Analytical chromatography method: mobile phase: 0-50% acetonitrile (100-50% water)/ 0-50 min, flow rate of 1 ml/min. The mass spectrometry analysis of DTX-P7 was shown in FIG. 3.

Structure 1

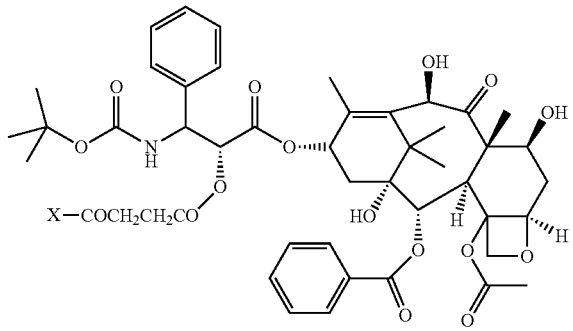

wherein —X is -LPLTPLP (SEQ ID No: 1), as the HSP90 inhibitory peptide;

Similar method was employed to prepare the PTX-P7 conjugate (Structure 2) by coupling paclitaxel with peptide, DOX-P7 (Structure 3) by coupling peptide at $NH_2$ of doxorubicin, and DOX—OH-P7 (Structure 4) at hydroxide radical.

Structure 2

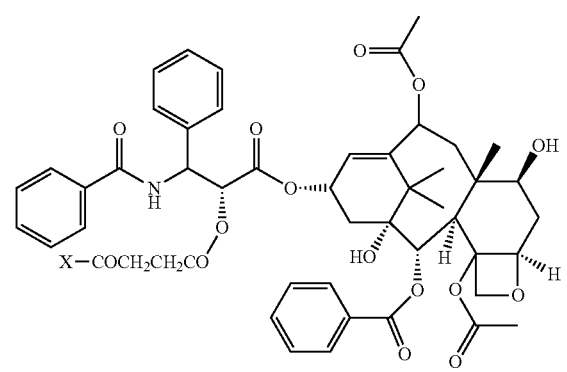

wherein —X is -LPLTPLP (SEQ ID No: 1), as the HSP90 inhibitory peptide;

Structure 3

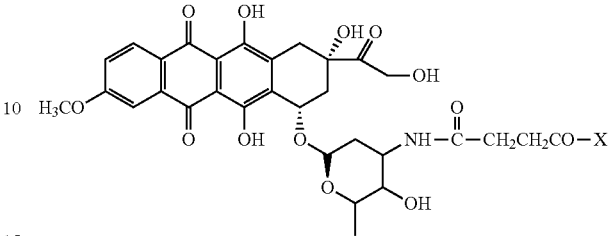

wherein —X is -LPLTPLP (SEQ ID No: 1), as the HSP90 inhibitory peptide;

Structure 4

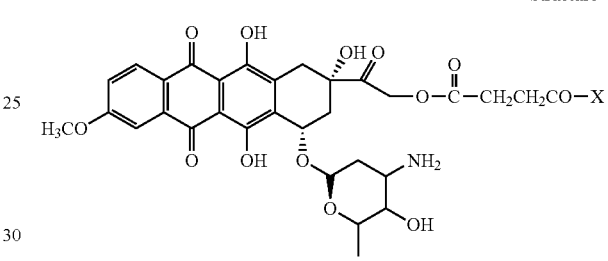

wherein —X is -LPLTPLP (SEQ ID No: 1), as the HSP90 inhibitory peptide

Embodiment 6: Establishment of Human Non-Small Cell Lung Cancer Xenograft Nude Mice Model A549 cell, a non-small cell lung cancer cell line, growing in logarithmic phase were collected and gently pipetted with 1 ml F-12K media containing 10% PBS to prepare the single cell suspension, which was consequently counted with appropriate dilution. The cell suspension was mixed with Matrigel (1:3) under ice bath. The concentration of the cell suspension was adjusted to $8 \times 10^6$ cells/ml and stored at 0° C. before transplantation.

Thirty BALB/c nu/nu female nude mice (16 g) were acclimated to the environment for 1 week before the formal experiment. When cell transplanted, A549 cell ($8 \times 10^5$ cells/ 100 II 1) was subcutaneously (s.c.) injected into the right side of the axilla of the animal after carefully disinfected with iodophor. State of the mice were observed before they were returned to rearing cage.

Embodiment 7: Nude Mice Grouping and Drug Administration

The mice were frequently observed and tumor volume was measured with a Vernier caliper, the volume was calculated by the equation (long diameter×short diameter$^2$) (½), when tumor reaching a size of 100 mm$^3$, mice were divided into 4 groups: (1) Saline (control), (2) DTX, (3) TN-DTX and (4) DTX-P7.

Next day after animal grouping, agents were administrated via intraperitoneal injection once a week for a total of four injections. The first administrated day was recorded as Day 0 and the other administrated days were respectively recorded as Day 7, Day 14, Day 21. The dosages are uniform 10 mg/kg based on the mass of DTX.

The mice were measured and weighted every two times a week. Tumor dimensions were measured using calipers. Tumor volume (V) and relative tumor volume (RTV) were calculated with the following equations:

$$V = \frac{1}{2} \times a \times b^2$$

(where a represents long diameter, b represents short diameter)

$$RTV = V_t/V_0$$

(where $V_0$ represents the tumor volume measured at first drug administration, Vt represents the tumor volume measured at t day)

The first day of the fifth week after the first injection, (28 day), the mice were sacrificed with an intraperitoneal injection of 0.5% pentobarbital sodium solution (50 mg/kg). The tumor tissues were resected and weighed. A part of tumor tissue was stored in 4% paraformaldehyde solution at 4° C. and the remaining part was stored at −80° C.

The body weight was also monitored during the in vivo studies and there was no significant difference in body weight among four groups indicating a good safety (FIG. 4) for all DTX preparation. The changes of tumor volumes of each group were showed in FIG. 5 and further presented as curve graph in FIG. 6. The results showed that all the DTX, DTX-P7, TN-DTX exerted obvious inhibitory effects on the tumor growth. DTX-P7 obviously inhibited the tumor growth. Particularly, DTX-P7 exhibited robust tumor regression with a significant difference compared with the CON group from the 4$^{th}$ day (p<0.05). The efficacy of DTX-P7 was superior to that of DTX, and the targeting nanodrug TN-DTX which was publicized in the inventor's previous patent (p<0.01). These data suggested that the inhibitory effects of DTX-P7 was not a simple superposition of DTX and targeting peptide, but a surprising suppressing effect. The inhibitory effects of DTX-P7 was remarkable compared with the previously publicized TN-DTX. Results showed that conjugate of HSP90 inhibitory peptide conjugating with DTX via linker present remarkable advantage for suppressing tumor growth when compared with the previously publicized nanodrug TN-DTX.

Embodiment 8: Cytotoxicity of Four Conjugates for Diverse Cancer Cells

Lung adenocarcinoma A549, breast cancer MCF-7S and melanoma A375 cells were diluted respectively to $3 \times 10^4$ cells/ml and pipetted to 96-well plate with 100 μl in each well. Twenty-four hours later, 5, 20, 80 or 320 nM DTX-P7, Paclitaxel-heptapeptide conjugate (PTX-P7), Doxorubicin-NH$_2$-heptapeptide conjugate (DOX-P7) and Doxorubicin-OH-heptapeptide conjugate (DOX-OH-P7) were added to the wells and incubated for 48 h. Then 10 μl CCK-8 was added and measured 1.5 h later at 450 nm to calculate the viability and median inhibitory concentration IC$_{50}$. Results in Table 1 showed that the four conjugates exerted excellent inhibitory effects to diverse tumor cells indicating a potential for a variety of cancer treatment.

TABLE 1 the cytotoxicity of four conjugates for diverse tumor cells (IC$_{50}$, nM)

| Tumor Cell | DTX-P7 | PTX-P7 | DOX-P7 | DOX-OH-P7 |
| --- | --- | --- | --- | --- |
| Lung A549 | 4.5 | 7.2 | 6.5 | 6.2 |
| Breast cancer MCF-7S | 11.7 | 16.2 | 23.3 | 18.1 |
| Melanoma A375 | 16 | 20.6 | 30.6 | 28.4 |

REFERENCES

1. Ferrarini M, Heltai S, Zocchi M R, Rugarli C. Unusual expression and localization of heat-shock proteins in human tumor cells. Int J Cancer 1992; 51:613-9.
2. Becker B, Multhoff G, Farkas B, Wild P J, Landthaler M, Stolz W, Vogt T., Induction of HSP90 protein expression in malignant melanomas and melanoma metastases. Exp. Dermatol. 2004; 13: 27-32.
3. Zhao R, Davey M, Hsu Y C, Kaplanek P, Tong A, Parsons A B, Krogan N, Cagney G, Mai D, Greenblatt J, Boone C, Emili A, Houry W A. Navigating the chaperone network: an integrative map of physical and genetic interactions mediated by the HSP90 chaperone. Cell 2005; 120: 715-727.

What is claimed is:

1. A conjugate, wherein the conjugate is a HSP90 inhibitory peptide conjugated to a cytotoxic agent via a linker,
the HSP90 inhibitory peptide for inhibiting HSP90 expression having an amino acid sequence of LPLTPLP (SEQ ID No: 1),
the cytotoxic agent is selected from docetaxel, paclitaxel or doxorubicin, and
the linker has the following general formula: —CO—(CH$_2$CH$_2$)$_n$—CO—, wherein n is selected from 1, 2, 3, 4, 5, 6, 7, 8, 9, or 10.

2. The conjugate according to claim 1, wherein
the amino terminal of the HSP90 inhibitory peptide is linked to 1-3 G(s), and
the carboxyl terminal of the HSP90 inhibitory peptide is linked to S, SH or SHS.

3. The conjugate according to claim 1, wherein
the linker is —CO—CH$_2$CH$_2$—CO—.

4. The conjugate according to claim 1, wherein the amino terminal of the HSP90 inhibitory peptide being connected to 2-OH of docetaxel or paclitaxel via the linker, or the amino terminal of the HSP90 inhibitory peptide being connected to -3-NH$_2$ on the 10-lyxo-hexopyranosyl group of the doxorubicin via the linker, or the amino terminal of the HSP90 inhibitory peptide being connected to 8-glycolyl group of the doxorubicin via the linker.

5. A conjugate, wherein the conjugate is selected from conjugates having the following chemical structures:

Structure 1

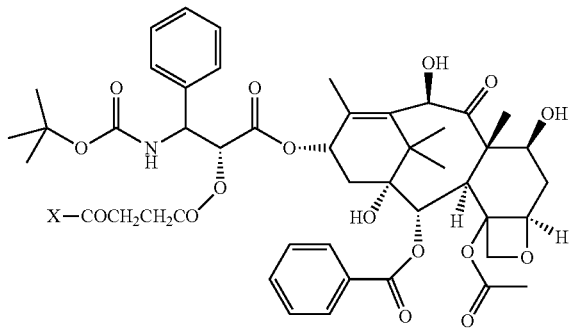

wherein —X is -LPLTPLP (SEQ ID No: 1), as the HSP90 inhibitory peptide;

Structure 2

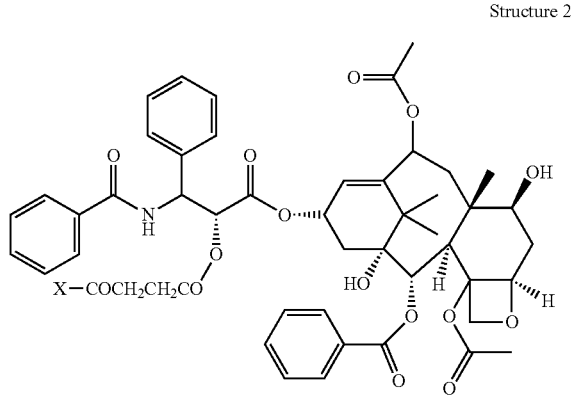

wherein —X is -LPLTPLP (SEQ ID No: 1), as the HSP90 inhibitory peptide;

Structure 3

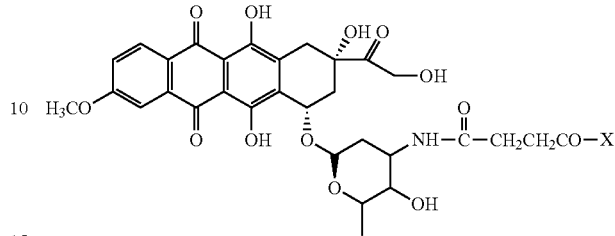

wherein —X is -LPLTPLP (SEQ ID No: 1), as the HSP90 inhibitory peptide;

Structure 4

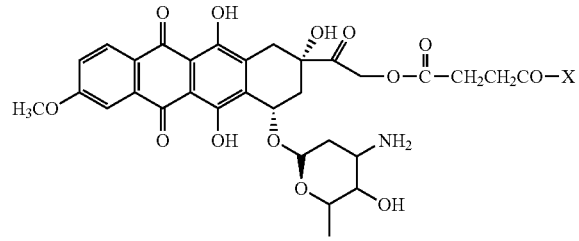

wherein —X is -LPLTPLP (SEQ ID No: 1), as the HSP90 inhibitory peptide.

6. A method of treatment of a tumor, comprising administering of an effective amount of a drug comprising the conjugate according to claim 1 to a subject.

7. The method according to claim 6, wherein the tumor is HSP90 highly-expressed tumor.

8. A tumor targeting agent for inhibiting tumor progress, comprising the conjugate according to claim 1 and pharmaceutically acceptable excipient.

9. The conjugate according to claim 1, wherein the HSP90 inhibitory peptide further has activities for promoting an apoptosis and inhibiting an autophagy.

10. The method according to claim 7, wherein the tumor is selected from lung cancer, lung adenocarcinoma, melanoma, gastric cancer, breast cancer, renal carcinoma, liver cancer, oral epidermoid carcinoma, cervical cancer, ovarian cancer, pancreatic cancer, prostate cancer, colorectal cancer and neural tumor.

11. The method according to claim 7, wherein the tumor is lung adenocarcinoma, breast cancer or melanoma.

12. The method according to claim 7, wherein the tumor is lung adenocarcinoma.

13. The method according to claim 7, wherein the amino terminal of the HSP90 inhibitory peptide is linked to 1-3 G(s), and the carboxyl terminal of the HSP90 inhibitory peptide is linked to S, SH or SHS.

14. The method according to claim 7, wherein the linker of the conjugate is —CO—CH$_2$CH$_2$—CO—.

15. The method according to claim 7, wherein the amino terminal of the HSP90 inhibitory peptide being connected to 2-OH of docetaxel or paclitaxel via the linker, or the amino terminal of the HSP90 inhibitory peptide being connected to -3-NH$_2$ on the 10-lyxo-hexopyranosyl group of the doxorubicin via the linker, or the amino terminal of the HSP90 inhibitory peptide being connected to 8-glycolyl group of the doxorubicin via the linker.

16. A method of treatment of a tumor, comprising administering of an effective amount of a drug comprising a conjugate to a subject, wherein the conjugate is selected from conjugates having the following chemical structures:

Structure 1

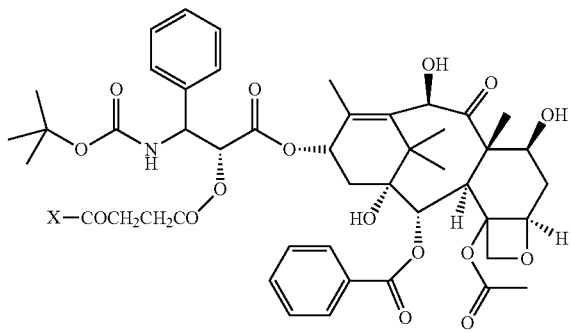

wherein —X is -LPLTPLP (SEQ ID No: 1), as the HSP90 inhibitory peptide;

Structure 2

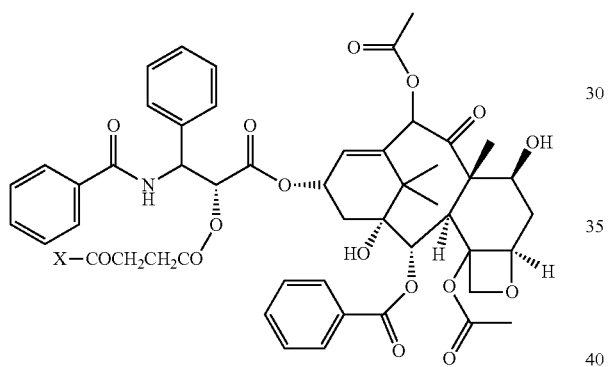

wherein —X is -LPLTPLP (SEQ ID No: 1), as the HSP90 inhibitory peptide;

Structure 3

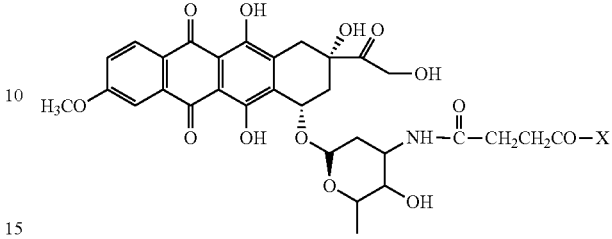

wherein —X is -LPLTPLP (SEQ ID No: 1), as the HSP90 inhibitory peptide;

Structure 4 wherein —X is -LPLTPLP (SEQ ID No: 1), as the HSP90 inhibitory peptide.

* * * * *

SEQUENCE LISTING

```
<160> NUMBER OF SEQ ID NOS: 1

<210> SEQ ID NO 1
<211> LENGTH: 7
<212> TYPE: PRT
<213> ORGANISM: ARTIFICIAL SEQUENCE
<220> FEATURE:
<223> OTHER INFORMATION: SYNTHESIZED

<400> SEQUENCE: 1

Leu Pro Leu Thr Pro Leu Pro
1               5
```